United States Patent [19]

Marshall

[11] 4,137,327

[45] Jan. 30, 1979

[54] PROCESS FOR WEIGHT REDUCTION

[76] Inventor: Edward M. Marshall, 700 Bonhill Rd., Los Angeles, Calif. 90049

[21] Appl. No.: 468,552

[22] Filed: May 9, 1974

[51] Int. Cl.$^2$ .................... A61K 31/16; A61K 31/165
[52] U.S. Cl. ..................................... 424/324; 424/320
[58] Field of Search ............................... 424/320, 324

[56] References Cited

U.S. PATENT DOCUMENTS 3,740,440   6/1973   Pober ................................... 424/320

OTHER PUBLICATIONS

Physician's Desk Reference (1971) pp. 1522-1523.
Merck Index, 8th Edition, 1968, pp. 28-29.
Goodman et al., Pharmacological Basis of Therapeutics (1965) pp. 379-384.

Primary Examiner—Albert T. Meyers
Assistant Examiner—D. W. Robinson

Attorney, Agent, or Firm—Edward D. O'Brian

[57] ABSTRACT

In the digestive tract certain nerve endings regulate the release of certain hormones in response to the movement of a quantity of food through the digestive tract. This release of hormones controls the operation of the pancreas in supplying to the intestinal tract certain digestive enzymes which are used in breaking down fats, proteins, and certain complex carbohydrates in the food as the quantity of food passes through the small intestine. It is possible to anesthesize these nerve endings prior to the consumption of such a quantity of food so as to inhibit the release of these hormones. As a consequence of this, a quantity of food moving through the digestive tract past these anesthesized nerve endings will not be subject to the action of these enzymes and will move through the small intestine without such types of materials contributing food energy or calories to the body. This can be utilized to accomplish a reduction in weight or to control weight.

9 Claims, No Drawings

PROCESS FOR WEIGHT REDUCTION

CROSS-REFERENCE TO RELATED APPLICATION

This application discloses and claims subject matter set forth in the abandoned Edward Marshall U.S. patent application Ser. No. 57,833, filed July 23, 1970, now abandoned entitled, "MEDICATION AND METHOD OF WEIGHT REDUCTION OR WEIGHT CONTROL BY INCREASING THE RATIO OF INGESTED TO DIGESTED FOOD STUFFS."

BACKGROUND OF THE INVENTION

The invention set forth in this specification pertains to a new and improved process for weight reduction.

It is commonly recognized that many individuals are unnecessarily and undesirably obese. The physical and psychological consequences of such obesity are so well established that it is not considered necessary to indicate them in detail in this specification. As a consequence of the recognition of the problems associated with unnecessary obesity a great deal of work has been devoted to the field of human weight reduction.

Probably the best established and least questionable method of causing weight reduction involves the simple expedient of having an individual consume less food than is required to sustain body weight. Normally, diets to achieve weight reduction in this manner specify that an individual shall consume comparatively limited quantities of various different foodstuffs as are necessary to maintain a balanced diet. This type of process for achieving weight reduction is frequently undesirable because it in effect semi-starves an individual. As a general rule the feeling of hunger which is normally associated with this method of weight control is undesirable.

In order to avoid the hungry feeling normally associated with dieting many individuals have proposed different types of specialized diets which are intended to avoid such a feeling. To the extent that they are effective such diets are considered to be effective in various different ways. Frequently such specialized diets restrict the amount of one or more essential nutrients consumed or require an individual to eat only one type of food. These diets are often unsatisfactory because they also require drastic changes in established eating habits and may even be unhealthy. Diets of this latter type which either restrict the consumption of one or more essential foodstuffs or permit an individual to only eat one type of foodstuff are considered to be detrimental by many medical authorities. The reasons for this primarily relate to the need for a balanced diet in order to keep the human body operating in a normal manner. Various types of medication have also been utilized so as to either directly or indirectly cause a loss in weight. Frequently, compounds such as various amphetamines have been utilized for this purpose because they tend to suppress the appetite. Other medicants such as diuretics, various thyroid preparations, digitalis and the like have often been utilized in order to accomplish weight reduction. In general, the use of medication to effect weight control is undesirable because of unwanted or side effects resulting from the use of various different compounds.

As a consequence of the limitations of the various methods of causing weight reduction indicated in this discussion, it is considered that there is a need for a new and improved method of causing weight reduction. It is also considered that there is a need for a new and improved method of weight reduction which will permit an individual to eat comparatively large or normal quantities of foods that are commonly consumed. This latter is quite important since it is frequently undesirable and/or virtually impossible to alter an individual's normal eating habits.

SUMMARY OF THE INVENTION

A basic objective of the invention is to provide a new and improved process or method for causing weight reduction. More specifically, the invention is intended to provide a method as indicated which is both safe and effective and which can be easily and conveniently carried out or practiced. The invention is also intended to provide a method as described which can be utilized without significantly altering the eating habits of an individual.

In accordance with this invention these objectives are achieved in a weight control process in which a quantity of food is consumed and passes through the digestive tract by the improvement which comprises: the quantity of food including foodstuffs requiring digestion caused by pancreatic enzymes for their absorption into the bloodstream from the small intestine, anesthetizing the nerve endings in the digestive tract which release hormones when contacted by food passing through the digestive tract so as to trigger the release of pancreatic enzymes into the digestive tract by the pancreas prior to this quantity of food contacting the nerve endings, these nerve endings being anesthesized to an extent effective to inhibit them from releasing sufficient hormones to cause the release of the pancreatic enzymes.

With the process of the present invention the anesthetization serves to prevent the release of the noted hormones when the nerve endings are contacted by the quantity of food. This has the effect of preventing significant release of the noted enzymes by the pancreas to the digestive tract. As a consequence of this the foodstuffs present in the quantity of food requiring digestion by pancreatic enzymes for absorption into the bloodstream pass through the digestive tract without being digested to a form in which they are capable of being absorbed into the bloodstream.

DETAILED DESCRIPTION

Because of its length a summary such as the preceding summary cannot be expected to adequately and completely indicate all facets of an invention such as the present invention. This invention is predicated upon an alternation in the usual digestion of food in the human digestive tract. An understanding of the invention requires a consideration of the normal operation of certain parts of the digestive tract and of certain parts of the body.

As food is consumed by an individual such food will be masticated and conveyed to the stomach. The time such food will stay in the stomach will vary greatly depending upon the quantity of food consumed at one time and the inherent nature of an individual. Normally, after an average sized meal and gastric emptying time—i.e., the time when a quantity or bolus of food remains in the stomach—is about forty minutes. The gastic emptying time of a stomach will, however, vary between comparatively wide limits in accordance with a large number of factors which are unimportant to a consideration of the present invention.

As a quantity or bolus of food moves through the stomach towards the pyloric valve controlling the discharge of food from the stomach it will pass a terminal region of the stomach known as the pyloric antrum. Various nerve endings which are critical as far as the invention is concerned are located in the wall of the stomach in this pyloric antrum area, in the area of the pyloric valve and in the area of the connected first portion of the duodenum. Corresponding nerve endings may also appear to a limited degree in what is referred to as the second portion of the duodenum.

The nerve endings which are referred to in the preceding play an important part in the normal digestion process. They serve to cause certain cells in the lining of the noted portions of the digestive tract to release the hormones secretin and pancreozymin into the bloodstream in response to a quantity or bolus of food moving through the digestive tract so as to contact or actuate these nerve endings. It is well known that the release of these hormones into the bloodstream results in these hormones being conveyed in the bloodstream to the pancreas.

When these hormones reach the pancreas they serve to actuate or trigger the pancreas into the production and rapid release of various pancreatic digestive enzymes and juices. Since such enzymes are well known it is not considered necessary to discuss them in detail in this specification. The enzymes produced by the pancreas are considered necessary for the digestion or conversion of certain types of foodstuffs to a form capable of absorption into the bloodstream through the walls of the small intestine. Thus, for example, enzymes of the lipase class are normally required to completely digest or hydrolyze these fats to glycerol and fatty acids.

The various pancreatic enzymes produced in response to the delivery of the hormones secretin and pancreozymin to the pancreas are, of course, conveyed from the pancreas by the pancreatic ducts to the lower or second portion of the duodenum. Here these enzymes are normally mixed with a quantity or bolus of food passing through the digestive tract. Normally the time required from the actuation of the noted nerve endings until these enzymes are admixed with material in the duodenum will reasonably approximate the time required for a quantity or bolus of food to travel from the pyloric valve to the area of the duodenum where these enzymes are passed into the digestive tract.

The normal movement of material within the digestive tract produced by muscular contraction will serve to mix these enzymes with food material present as they are introduced into the duodenum to a sufficient extent so that various foodstuffs in the food material acted upon by these enzymes will be reduced to a form capable of absorption into the bloodstream through the walls of the intestine before the food material is evacuated from the body at the lower end of the digestive tract. The digestive process is, of course, much more complicated and detailed than is indicated by this discussion.

A more complete discussion of the digestive processes within the human body is interesting from an academic standpoint but is unnecessary for an understanding of the present invention. This invention is primarily concerned with weight reduction resulting from a lack of digestion in the intentinal tract of foodstuffs which require digestion by pancreatic enzymes in order to contribute food values or calories to the human body. Thus, the invention does not affect certain foodstuffs such as comparatively simple sugars which do not have to be digested in order to be taken up or absorbed into the bloodstream.

In accordance with this invention the nerve endings controlling the release of hormones to trigger the operation of the pancreas are anesthesized through the use of a topically effective local anesthetic so that when these nerve endings are contacted by a quantity or bolus of food after being anesthesized they do not cause the release of the hormones secretin and pancreozymin. This in turn has the effect of preventing the pancreas from releasing digestive enzymes into the digestive tract. As a consequence of this foodstuffs requiring digestion by such enzymes in order to be placed in a form to pass into the bloodstream are not digested by these enzymes. Hence, they pass through the body without contributing energy values of the bloodstream.

The method of anesthesizing the nerve endings referred to in the preceding is considered to be interesting from a technical standpoint. Because of the location of these nerve endings obviously conventional methods of administering anesthetics such as injection or the like cannot be utilized. It is preferred with the present invention to utilize a topically effective local anesthetic orally in the form of a means for releasing the anesthetic so that it will be operative for its intended purpose and/or released for its intended purpose in the areas of the digestional tract where the noted nerve endings are located.

Virtually any known anesthetic which can be released or utilized in such areas can be used with the invention. It is presently considered preferable to utilize the anesthetic oxethazaine since this anesthetic is considered to be effective, and since it is conveniently available. As indicated by the article by Glassman, et al. entitled *ACUTE AND CHRONIC TOXICITY OF OXETHAZAINE: A HIGHLY POTENT LOCAL ANESTHETIC* appearing in "Toxicology and Applied Pharmacology 5,184–200 (1963)" this anesthetic is a potent local anesthetic which effectively will penetrate the lipids of nerve sheaths to effect adequate, relatively prolonged anesthesia at comparatively low pH's such as are found in the digestional tract in the areas where the noted nerve endings are located.

The fact that this anesthetic is safe for use with the human body is indicated by its current commercial usage in an oral form in the treatment of certain types of stomach disorders. As this anesthetic is used for such purposes it has not been intended to be effective and has not been effective for weight control. The article by Slayback, et al. entitled *THE PANCREATIC SECRETORY RESPONSE TO TOPICAL ANESTHETIC BLOCK OF THE SMALL BOWEL* appearing on pages 591 to 595 of the April 1967 issue of "Surgery" is considered to demonstrate the acceptability of oxethazaine for use with the invention.

It is not to be assumed from the aforegoing that this is the only desirable or usable anesthetic for use with the invention. It is considered that acceptable results can be achieved with other related anesthetics such as lidocaine. Since many such other local anesthetics are well known to the medical field it is considered that it is unnecessary to specifically recite a long list of them in this specification. Many such local anesthetics are indicated in materials of record in connection with the aforenoted prior application.

In order to achieve the results of the invention it is considered normally necessary to utilize a local anesthetic as indicated in connection with a coating which will block the action of the anesthetic and/or the release of the anesthetic until the anesthetic and the coating material have reached the mid-position of the stomach. Such a coating may conveniently take the form of a gelatin capsule located around the anesthetic used. Similarly the anesthetic may be encapsulated in small spheres of this or other known coatings. Many such coating materials are known and used. Various different fats, fatty acids, waxes and other various naturally occurring and artificial hydrocolloids, including common vegetable gums, various starch derivatives and the like can be utilized as coatings for either a large quantity of an anesthetic or the formation of various small coated spheres of an anesthetic.

The anesthetic covered by a coating to accomplish controlled or limited release as indicated may be in a form of a pure compound of the anesthetic used or in the form of a non-toxic solution or mixture of the anesthetic. In many cases, it may prove beneficial to utilize compressed tablets of an anesthetic as indicated in practicing this invention. Such a tablet may, if desired, be covered with a coating as indicated. Also, an anesthetic in such a tablet may be admixed with any of the materials indicated in this specification as being usable with an anesthetic as described.

Many of such coating materials are useful in serving secondary functions in carrying out the process of the invention. One function relates to at least the temporarily adhering of an anesthetic as noted in a coating on the interior of the pyloric antrum, the pyloric valve region, and to at least the first portion of the duodenum so as to insure sufficient contact between these areas of the interior of the body and the anesthetic to insure that the anesthetic is operative for its intended purpose. To achieve this result a coating as used must not only release an anesthetic after it has travelled through the initial portions of the digestive tract as noted, but also must tend to adhere to the noted areas in the digestive tract so as to hold or "fix" the anesthetic in an operative position to anesthesize the noted nerve endings.

Another function which can be exercised by such coating materials relates to regulating the rate at which an anesthetic of the type noted can be released in the digestive tract. Frequently, it will be undesirable for a significant quantity of the anesthetic to be released at one time since this is apt to cause various side effects. Further, if all of the anesthetic used is released at one time there is a distinct possibility that the anesthetic employed will not be distributed over substantially all of the areas to be anesthesized in accordance with this invention.

If desired, the anesthetic may be mixed with a separate adhesive type or adherent type of material such as albumin in a capsule or the like to insure that the anesthetic will be adhered to the interior of the digestive tract where the noted nerve endings are located so that the anesthetic will exercise its desired effect in anesthesizing such nerve endings. In general, effective results can be achieved using from about 1 to about 100 volumes of albumin or a similar agent per volume of anesthetic employed. To a degree, common alumina gel may be used as a somewhat effective, separate adherent agent to assist in the adherence of an anesthetic in an operative location. Various materials as indicated in this paragraph are also considered desirable in achieving a controlled release of anesthetic so as to prevent rapid absorption of anesthetic into the bloodstream.

The amount of the anesthetic which should be used in practicing the invention may be varied over comparatively wide limits. It is presently considered that the amount of anesthetic which should be used by a normal adult will normally be within the range of from about 200 to about 800 milligrams per application. It is also considered, however, that effective results can normally be achieved using from about 50 to about 2,000 milligrams of anesthetic per application. An amount of anesthetic as used is considered effective when it is effective to anesthesize sufficient nerve endings to as to block the delivery of at least half of the normal quantity of pancreatic enzymes which are normally produced in response to the consumption of the quantity or bolus of food.

An anesthetic as indicated should be taken on an empty or nearly empty stomach a sufficient time prior to food being consumed so that the noted nerve endings will be anesthesized when food reaches them. Such a period of time will, of course, be related to the gastric emptying time of a particular individual. As indicated in the preceding there can be a significant variation in such a gastric emptying time.

For some individuals the requirement that the anesthetic be taken at a time interval prior to food reaching the nerve endings governing the release of the hormones secretin and pancreozymin which is effective so that these nerve endings will be anesthesized when the food reaches them will make it necessary that the anesthetic be taken substantially contemporaniously with the consumption of food; for others it will make it necessary that the anesthetic be taken an hour or more prior to the consumption of food. It is considered that normally an anesthetic as described should be taken from about 30 to about 60 minutes prior to the consumption of a meal.

One of the unique features of this invention lies in the fact that no significant harm can result if either the anesthetic is taken at an improper time or if for some reason or another the anesthetic is released in the digestive tract slightly before or beyond the areas in the digestive tract where the noted nerve endings are located. If the anesthetic is taken at an improper time the only consequence is that all the foodstuffs in a quantity or bolus of food consumed will be digested in the conventional manner. If the anesthetic is for one reason or another released into the stomach so as to anesthesize other than the noted nerve endings no significant problems will arise. In this connection it is noted that the anesthetic oxethazaine is commonly taken orally in the treatment of stomach conditions. Similarily, because of the nature of the duodenum and the remainder of the intestinal tract no harm will result if the anesthetic used is released generally beyond the areas where the noted nerve endings are located in the digestive system.

In general, the process of this invention is primarily effective in preventing the body from utilizing nutrient values in comparatively complex foodstuffs. For this reason the use of the process of this invention in weight reduction requires little or no control of food consumed. In practicing the invention it is best to avoid the consumption of easily absorbed foodstuffs such as simple sugars which will pass directly into the bloodstream to as great an extent as reasonably possible. Because the invention is primarily significant with comparatively complex foodstuffs, it is considered that some individuals being treated in accordance with the invention be given an appropriate dietary supplement of fat soluble vitamins and other materials necessary for good health when the invention is not being practiced.

I claim:

1. In a weight control process in which a quantity of food is consumed and passes through the gastro intestinal digestive tract of a living body:

said quantity of food including foodstuffs requiring digestion caused by pancreatic enzymes for absorption into the bloodstream from the small intestine, the improvement which comprises periodically anesthesizing the nerve endings in the digestive tract which release hormones when contacted by food passing through the digestive tract so as to trigger the release of said pancreatic enzymes into the digestive tract by the pancreas prior to said quantity of food contacting said nerve endings only prior to the passage of food into said digestive tract, said anesthetization being carried out to an extent effective and at a time effective to inhibit said nerve endings from releasing sufficient hormones to cause the release of said pancreatic enzymes which will contact said food as it passes through the digestive tract, said anesthetization serving to prevent the release of said hormones when said nerve endings are contacted by said quantity of food, this having the effect of preventing release of said enzymes by the pancreas to the digestive tract so that said food passes through the digestive tract without being digested so that it is capable of being absorbed into the bloodstream as a consequence of the absence of said enzymes 2. A weight control process as claimed in claim 1 wherein:

said nerve endings are anesthesized by orally taking a quantity effective to cause said inhibition of an anesthetic means coated with a coating means which is effective to delay the release of said anesthetic means until said anesthetic means reaches the vicinity of said nerve endings in the digestive tract.

3. A weight control process as claimed in claim 2 wherein:

said anesthetic means is oxethazaine.

4. A weight control process as claimed in claim 2 wherein:

said anesthetic means is orally taken with an adherence means for causing said anesthetic means to adhere to the interior of the digestive tract.

5. A weight control process as claimed in claim 4 wherein:

said adherence means is albumin and is admixed with said anesthetic means, said anesthetic means and said albumin both being coated with said coating means.

6. A weight control process as claimed in claim 2 wherein:

from about 50 to about 2,000 milligrams of said anesthetic means are taken at one time, said time being prior to food being taken into the digestive tract.

7. A weight control process as claimed in claim 2 wherein:

from about 200 to about 800 milligrams of said anesthetic means are taken at one time, said time being prior to food being taken into the digestive tract.

8. A weight control process as claimed in claim 1 wherein:

said nerve endings are anesthesied by orally taking a quantity effective to cause said inhibition of an anesthetic means coated with a coating which will delay the release of said anesthetic means until said anesthetic means reaches the vicinity of said nerve endings in the digestive tract, said anesthetic means is oxethazaine, and from about 50 to about 2,000 milligrams of said anesthetic means are taken at one time, said time being prior to food being taken into the digestive tract.

9. A weight control process as claimed in claim 8 wherein:

said anesthetic means is orally taken with adherence means for causing said anesthetic to adhere to the interior of the digestive tract, and said adherence means is albumin and is admixed with said anesthetic, said anesthetic and said albumin both being coated with said coating.